United States Patent
Skodda

(10) Patent No.: US 11,504,416 B2
(45) Date of Patent: *Nov. 22, 2022

(54) FORMULATION WITH CANNABINOIDS

(71) Applicant: Anja Skodda, Venice, CA (US)

(72) Inventor: Anja Skodda, Venice, CA (US)

(73) Assignee: PAW POWER, INC., Venice, CA (US)

(*) Notice: Subject to any disclaimer, the term of this patent is extended or adjusted under 35 U.S.C. 154(b) by 56 days.

This patent is subject to a terminal disclaimer.

(21) Appl. No.: 16/930,454

(22) Filed: Jul. 16, 2020

(65) Prior Publication Data

US 2020/0345816 A1 Nov. 5, 2020

Related U.S. Application Data

(63) Continuation-in-part of application No. 16/560,565, filed on Sep. 4, 2019, now Pat. No. 11,191,814.

(60) Provisional application No. 62/726,467, filed on Sep. 4, 2018.

(51) Int. Cl.

| | | |
|---|---|---|
| A61K 38/39 | (2006.01) | |
| A61K 9/00 | (2006.01) | |
| A61K 31/728 | (2006.01) | |
| A61K 31/7008 | (2006.01) | |
| A61K 31/375 | (2006.01) | |
| A61K 31/593 | (2006.01) | |
| A61K 31/352 | (2006.01) | |
| A23L 33/105 | (2016.01) | |
| A23L 33/17 | (2016.01) | |
| A23L 33/125 | (2016.01) | |
| A23L 33/15 | (2016.01) | |
| A61K 31/355 | (2006.01) | |

(52) U.S. Cl.
CPC ............ *A61K 38/39* (2013.01); *A23L 33/105* (2016.08); *A23L 33/125* (2016.08); *A23L 33/15* (2016.08); *A23L 33/17* (2016.08); *A61K 9/0056* (2013.01); *A61K 31/352* (2013.01); *A61K 31/355* (2013.01); *A61K 31/375* (2013.01); *A61K 31/593* (2013.01); *A61K 31/7008* (2013.01); *A61K 31/728* (2013.01); *A23V 2002/00* (2013.01)

(58) Field of Classification Search
CPC .... A61K 38/39; A61K 9/0056; A61K 31/352; A61K 31/355; A61K 31/375; A61K 31/593; A61K 31/7008; A61K 31/728; A23L 33/17; A23L 33/105; A23L 33/125; A23L 33/15; A23V 2002/00
USPC ........................................................ 514/54
See application file for complete search history.

(56) References Cited

U.S. PATENT DOCUMENTS

| | | | |
|---|---|---|---|
| 8,211,946 B2 | 7/2012 | Whittle | |
| 8,435,556 B2 | 5/2013 | Stinchcomb | |
| 11,191,814 B2 * | 12/2021 | Skodda | ................ A23K 20/174 |
| 2002/0025921 A1 | 2/2002 | Petito | |
| 2004/0034108 A1 | 2/2004 | Whittle | |
| 2004/0138293 A1 | 7/2004 | Werner | |
| 2008/0003270 A1 | 1/2008 | Garcia Martinez | |
| 2008/0139667 A1 | 6/2008 | Robson | |
| 2011/0171187 A1 | 7/2011 | Moore | |
| 2014/0302121 A1 | 10/2014 | Bevier | |
| 2015/0132402 A1 | 5/2015 | Moore et al. | |
| 2015/0197484 A1 | 7/2015 | Stinchcomb | |
| 2016/0213027 A1 | 7/2016 | Maniatakos | |
| 2016/0303162 A1 | 10/2016 | Minatelli | |
| 2016/0361290 A1 | 12/2016 | Robson | |
| 2020/0069776 A1 | 3/2020 | Skodda | |

FOREIGN PATENT DOCUMENTS

| | | |
|---|---|---|
| EP | 1765314 B1 | 3/2007 |
| JP | 2016025870 A | 2/2016 |
| KR | 1020060006057 A | 10/2005 |
| KR | 20060086396 A | 7/2006 |
| WO | 2003034993 A2 | 5/2003 |
| WO | 2004016246 A1 | 2/2004 |
| WO | 2007148739 A1 | 12/2007 |
| WO | 2020060761 A9 | 3/2020 |

OTHER PUBLICATIONS

Kevin J. Ruff, et al., "Safety evaluation of a natural eggshell membrane-derived product," Food and Chemical Toxicology, 2012, pp. 604-611, 50.
Glossary of Medical Education Terms, Institute of International Medical Education, accessible at: http://www.iime.org/glossary.htm, (accessed in 2013).
Joerg Jerosch, "Effects of glucosamine and chondroitin sulfate on cartilage metabolism in OA: Outlook on other nutrient partners especially omega-3 fatty acids," International Journal of Rheumatology, 2011, pp. 1-17, vol. 2011.
Written Opinion of the International Searching Authority, dated May 12, 2020, for corresponding PCT Application No. PCT/US19/49522, International Filing Date Sep. 4, 2019, consisting of 7 Pages.
International Search Report, dated May 12, 2020, for corresponding PCT Application No. PCT/US19/49522, International Filing Date Sep. 4, 2019, consisting of 2 Pages.

(Continued)

*Primary Examiner* — Yih-Horng Shiao
(74) *Attorney, Agent, or Firm* — Gearhart Law LLC; David Postolski

(57) ABSTRACT

A food supplement comprising a therapeutically effective amount of a composition is described. The composition includes hydrolyzed collagen, hyaluronic acid, ascorbic acid, and glucosamine hydrochloride. The composition may also include a cannabinoid or prodrug, vitamin C, vitamin D, and/or vitamin E. The therapeutically effective amount of the composition is effective in alleviating at least one symptom of a degenerative joint disease in a human or may be used for the prophylaxis of the degenerative joint disease in the human. The at least one symptom of the degenerative joint disease in the human includes joint pain and mobility pain.

20 Claims, 4 Drawing Sheets

(56) References Cited

OTHER PUBLICATIONS

"Cannabis for Pets—Benefits and Dangers," Happy Dog Food Rawlicious Nutrition Blog, Jul. 8, 2016, Retrieved on May 30, 2020, Retrievable at: https://happydogfood.com/blogs/news/cannabis-for-pets-benefits-and-dangers.

Simone Fuchs, "Automated 3D cultivation of primary chondrocytes in the pannus model," BioSpektrum, Jan. 2004, pp. 693-694.

Michael Schunck, "The Effectiveness of Specific Collagen Peptides on Osteoarthritis in Dogs—Impact on Metabolic Processes in Canine Chondrocytes," Journal of Animal Sciences, 2017, 7, pp. 254-266.

* cited by examiner

FORMULATION WITH CANNABINOIDS

CROSS-REFERENCE TO RELATED APPLICATIONS

This application is a U.S. Continuation-in-Part (CIP) Patent Application that claims priority to U.S. Non-Provisional patent application Ser. No. 16/560,565 filed on Sep. 4, 2019, which claims priority to U.S. Provisional Patent Application No. 62/726,467 filed on Sep. 4, 2018, the contents of which are hereby incorporated by reference in their entirety.

FIELD OF THE EMBODIMENTS

The field of the invention and its embodiments relate to food supplements comprising a therapeutically effective amount of a composition. In particular, the present invention and its embodiments relate to food supplements comprising a therapeutically effective amount of a composition that is effective in alleviating at least one symptom of a degenerative joint disease in a human or may be used for the prophylaxis of the degenerative joint disease in the human. The at least one symptom of the degenerative joint disease in the human includes joint pain and mobility pain.

BACKGROUND OF THE EMBODIMENTS

Arthropathy, or any disease of the joints, includes arthritis, Charcot joint, and diabetic hand syndrome. Symptoms of arthropathy include joint inflammation, joint deterioration because of nerve damage, and limited movement. Degenerative joint diseases include, but are not limited to, osteochondrosis and degenerative arthritis (or osteoarthritis). Symptoms of degenerative joint disease include joint swelling, muscle atrophy, pericapsular fibrosis, and crepitation. Degenerative joint disease can occur at any joint in the human's body, without limitation.

Osteochondrosis is a self-limiting developmental derangement of normal bone growth, primarily involving the centers of ossification in the epiphysis. It usually begins in childhood as a degenerative or necrotic condition. By definition, osteochondrosis is an aseptic ischemic necrosis. Degenerative arthritis (or osteoarthritis) is a type of arthritis that occurs when flexible tissue at the ends of bones wears down. The wearing down of the protective tissue at the ends of bones (e.g., cartilage) occurs gradually and worsens over time. Treatments for any such disease of the joints include medications (such as nonsteroidal anti-inflammatory drugs (NSAIDS)), physical therapy, and surgery. Thus, what is needed is a food supplement comprising a therapeutically effective amount of a composition that is effective in alleviating at least one symptom of a degenerative joint disease in a human or may be used for the prophylaxis of the degenerative joint disease in the human.

Review of Related Technology

JP 2016025870 A discloses an edible polymer hydrogel orally administered prior to or during a meal for weight control and glycemic control.

KR 20060086396 A and KR 1020060006057 A disclose cannabinoid receptor ligands for the treatment of diseases linked to the mediation of the cannabinoid receptors in animals.

WO 2007/148739 A1 discloses a cell activator, an anti-aging agent and an extracellular matrix production promoter, characterized by containing a plant extract containing a polyamine as an active ingredient in a cosmetic, a quasi-drug (such as an external preparation for skin, a bath agent or a hair growth agent), a food or drink or a pharmaceutical product.

U.S. Published Patent Application No. 2014/0302121 A1 describes a composition comprising a cannabinoid receptor binding agent contained in a particle for the treatment of skin conditions. The particle may be a nanoparticle, such as nanocrystalline cellulose. The particle may further be modified with functional moieties. Drug delivery properties may be modified by coating the particles or using vesicles to deliver the cannabinoid receptor binding agent and particle. A substrate may be used to deliver the composition to the skin.

U.S. Published Patent Application No. 2015/0197484 A1 describes microneedle drug delivery systems comprising a pharmaceutical compositions comprising pharmaceutically active agents (e.g., cannabidiol and prodrugs of cannabidiol) and microneedle arrays suitable for local and systemic delivery of the active agent to a mammal. This reference also describes methods of using a microneedle transdermal or topical drug delivery systems comprising pharmaceutical compositions, comprising cannabidiol and prodrugs of cannabidiol, and microneedle arrays in the treatment disease, including pancreatitis and pancreatic cancer.

U.S. Pat. No. 8,435,556 B2 describes a drug delivery systems for delivering cannabinoids transdermally. Preferably, the cannabinoids are delivered via an occlusive body (i.e., a patch) to alleviate harmful side effects and avoid gastrointestinal (first-pass) metabolism of the drug by the patient. A first aspect of the invention provides a method for relieving symptoms associated with illness or associated with the treatment of illness in a mammalian subject, comprising the steps of selecting at least one cannabinoid from the group consisting of cannabinol, cannabidiol, nabilone, levonantradol, (−)-HU-210, (+)-HU-210, 11-hydroxy-$\Delta$9-THC, $\Delta$8-THC-11-oic acid, CP 55,940, and R(+)-WIN 55,212-2, selecting at least one permeation enhancer from the group consisting of propylene glycol monolaurate, diethylene glycol monoethyl ether, an oleoyl macrogolglyceride, a caprylocaproyl macrogolglyceride, and an oleyl alcohol, and delivering the selected cannabinoid and permeation enhancer transdermally to treat an illness.

U.S. Published Patent Application No. 2016/0361290 A1 describes cannabinoids for the treatment of pain, inflammation and/or disease modification in arthritis. Preferably the cannabinoids are selected from cannabidiol (CBD) or cannabidivarin (CBDV) and delta-9-tetrahydrocannabinol (THC) or tetrahydrocannabinovarin (THCV). More preferably the cannabinoids are in a predefined ratio by weight of less than or equal to 19:1 of CBD or CBDV to THC or THCV.

U.S. Pat. No. 8,211,946 B2 describes pharmaceutical formulations, and more particularly to formulations containing cannabinoids for administration via a pump action spray. In particular, the invention relates to pharmaceutical formulations, for use in administration of lipophilic medicaments via mucosal surfaces, comprising: at least one lipophilic medicament, a solvent and a co-solvent, wherein the total amount of solvent and co-solvent present in the formulation is greater than 55% wt/wt of the formulation and the formulation is absent of a self-emulsifying agent and/or a fluorinated propellant.

U.S. Published Patent Application No. 2004/0034108 A1 relates to pharmaceutical formulations, and more particularly to formulations containing cannabinoids for administration via a pump action spray. In particular, the invention relates to pharmaceutical formulations, for use in administration of lipophilic medicaments via mucosal surfaces, comprising: at least one lipophilic medicament, a solvent and a co-solvent, wherein the total amount of solvent and co-solvent present in the formulation is greater than 55% wt/wt of the formulation and the formulation is absent of a self-emulsifying agent and/or a fluorinated propellant.

U.S. Published Patent Application No. 2004/0138293 A1 relates to a pharmacologically active composition which is suitable for use in palliative cancer therapy and as an agent having a muscle-relaxing and/or analgesic effect in neurological diseases. Said composition contains at least 80 wt. %, preferably 90 wt. %, tetrahydrocannabinol (THC) and cannabidiol (CBD), in relation to the overall weight of cannabinoids present therein. The weight ratio of THC to CBD=75:25-20:80, preferably 3:1-1:2, and especially 2:1. Said composition can be used for the production of pharmacologically effective agents which can be used in palliative cancer therapy and in the treatment of neurological diseases.

U.S. Published Patent Application No. 2008/0139667 A1 relates to the use of a combination of cannabinoids for the treatment of pain, inflammation and/or disease modification in arthritis. Preferably the cannabinoids are selected from cannabidiol (CBD) or cannabidivarin (CBDV) and delta-9-tetrahydrocannabinol (THC) or tetrahydrocannabinovarin (THCV). More preferably the cannabinoids are in a predefined ratio by weight of less than or equal to 19:1 of CBD or CBDV to THC or THCV.

EP 1,765,314 A1 relates to the use of a combination of cannabinoids for the treatment of pain, inflammation and/or disease modification in arthritis. Preferably the cannabinoids are selected from cannabidiol (CBD) or cannabidivarin (CBDV) and delta-9-tetrahydrocannabinol (THC) or tetrahydrocannabinovarin (THCV). More preferably the cannabinoids are in a predefined ratio by weight of less than or equal to 19:1 of CBD or CBDV to THC or THCV.

WO 2004/016246 A1 relates to pharmaceutical formulations, and more particularly to formulations containing cannabinoids for administration via a pump action spray. In particular, the invention relates to pharmaceutical formulations, for use in administration of lipophilic medicaments comprising one or more cannabinoids via mucosal surfaces, comprising: at least one lipophilic medicament which comprises one or more cannabinoids, a solvent and a co-solvent, wherein the total amount of solvent and co-solvent present in the formulation is greater than 55% wt/wt of the formulation, the formulation is absent of a self-emulsifying agent and/or a fluorinated propellant, and the cannabinoid(s) is/are present in the formulation in an amount greater than 10 mg/ml.

Various cannabinoid formulations exist in the art. However, these other formulations fail to solve all the problems taught by the present disclosure.

SUMMARY OF THE EMBODIMENTS

The present invention and its embodiments relate to food supplements comprising a therapeutically effective amount of a composition. In particular, the present invention and its embodiments relate to food supplements comprising a therapeutically effective amount of a composition that is effective in alleviating at least one symptom of a degenerative joint disease in a human or may be used for the prophylaxis of the degenerative joint disease in the human. The at least one symptom of the degenerative joint disease in the human includes joint pain and mobility pain.

A first embodiment of the present invention describes a food supplement for a human comprising a therapeutically effective amount of a composition. The composition includes hydrolyzed collagen, hyaluronic acid, glucosamine hydrochloride, and ascorbic acid. The therapeutically effective amount of the composition is effective in alleviating at least one symptom of a degenerative joint disease in a human (such as joint pain and mobility pain). In some examples, the composition further comprises a cannabinoid or prodrug thereof.

A second embodiment of the present invention describes a method to alleviate at least one symptom of a degenerative joint disease in a human or for the prophylaxis of the degenerative joint disease in the human. The method comprises administering a food supplement comprising: an extracellular matrix composition and a vitamin composition. The vitamin composition may include hyaluronic acid and at least one of vitamin C, vitamin D, and vitamin E. The extracellular matrix composition comprises hyaluronic acid, hydrolyzed collagen; and glucosamine or pharmaceutically acceptable salts thereof. In some examples, the food supplement further comprises a cannabinoid or prodrug thereof.

A third embodiment of the present invention describes a method to create a food supplement effective at alleviating at least one symptom of a degenerative joint disease in a human or for the prophylaxis of the degenerative joint disease in the human. The method comprises engaging in enzymatic hydrolysis of a collagen with a protease to create a hydrolyzed collagen and adding a formulation to the hydrolyzed collagen to create the food supplement.

The enzymatic hydrolysis of the collagen with the protease to create the hydrolyzed collagen comprises the following process steps: washing and drying mammal shavings (such as pigskin shavings), soaking the mammal shavings in approximately nine-fold water (w/v) at a first temperature of approximately 60° C. for a first time period of approximately 30 minutes to create a solution and to slightly denature collagen fibers of the mammal shavings, and adjusting a pH of the solution with 1 M hydrochloric acid (HCl) or 1 M sodium hydroxide (NaOH).

The enzymatic hydrolysis of the collagen with the protease to create the hydrolyzed collagen further comprises: adding an amount of the protease to the solution in a range between approximately 700 U/g of the mammal shavings to approximately 800 U/g of the mammal shavings, hydrolyzing the solution at a second temperature (e.g., an optimal temperature for the protease) and for a second time period of approximately 4 hours, terminating the hydrolysis by inactivating the protease at a fourth temperature of approximately 100° C. for a fourth time period of approximately 5 minutes, cooling the solution, adjusting the pH of the solution to a pH of 7, filtering the solution, dialyzing the filtrate at a third temperature (e.g., room temperature) for a third time period of approximately 48 hours, and obtaining the hydrolyzed collagen via freeze-drying.

The formulation comprises hyaluronic acid, glucosamine hydrochloride, and a vitamin composition. The vitamin composition may include vitamin C, vitamin D, and/or vitamin E. The formulation may also include a cannabinoid or prodrug thereof.

In general, the present invention succeeds in conferring the following benefits and objectives.

It is an object of the present invention to provide a food supplement for a human comprising a therapeutically effective amount of a composition.

It is an object of the present invention to provide a food supplement for a human comprising a therapeutically effective amount of a composition, where the composition includes hydrolyzed collagen, hyaluronic acid, glucosamine hydrochloride, and ascorbic acid.

It is an object of the present invention to provide a food supplement for a human comprising a therapeutically effective amount of a composition, where the composition includes hydrolyzed collagen, hyaluronic acid, glucosamine hydrochloride, ascorbic acid, and a cannabinoid or prodrug thereof.

It is an object of the present invention to provide a food supplement for a human that includes an extracellular matrix and a vitamin composition, where the extracellular matrix comprises hyaluronic acid, hydrolyzed collagen, and glucosamine or pharmaceutically acceptable salts thereof.

It is an object of the present invention to provide a food supplement for a human that includes an extracellular matrix, a vitamin composition, and a cannabinoid or prodrug thereof, where the extracellular matrix comprises hyaluronic acid, hydrolyzed collagen, and glucosamine or pharmaceutically acceptable salts thereof.

It is an object of the present invention to provide a food supplement for a human comprising a therapeutically effective amount of a composition, where the therapeutically effective amount of the composition is effective in alleviating at least one symptom of a degenerative joint disease in a human.

It is an object of the present invention to provide a method to alleviate at least one symptom of a degenerative joint disease in a human or for the prophylaxis of the degenerative joint disease in the human.

It is an object of the present invention to provide a method to create a food supplement effective at alleviating at least one symptom of a degenerative joint disease in a human or for the prophylaxis of the degenerative joint disease in the human.

It is an object of the present invention to provide a method for enzymatic hydrolysis of collagen with a protease to create hydrolyzed collagen.

DESCRIPTION OF THE PREFERRED EMBODIMENTS

Figure 1:
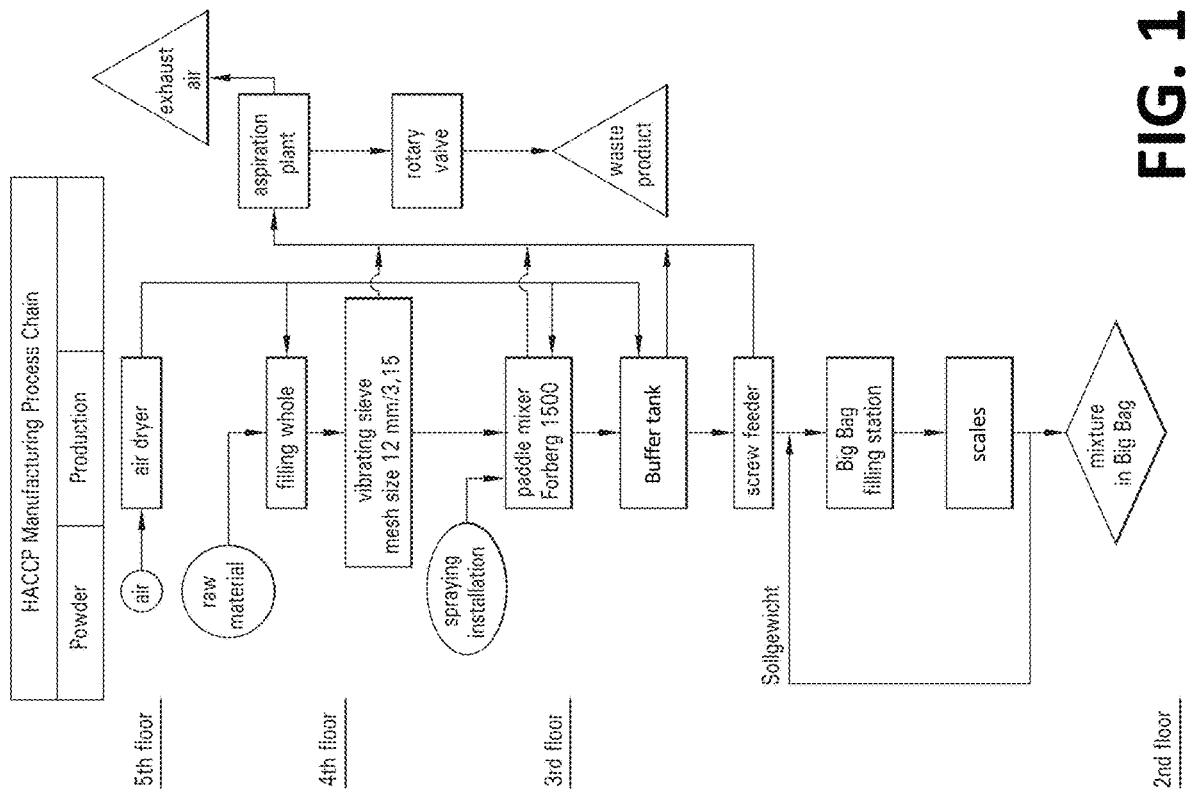
FIG. 1 depicts a hazard analysis and critical control point (HACCP) manufacturing process chain for mixing ingredients of the disclosed food formulation, according to at least some embodiments described herein.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

As used herein, the singular forms "a," "an," and "the," are intended to include the plural forms as well, unless the context clearly indicates otherwise.

The phrase "and/or," as used herein in the specification and in the claims, should be understood to mean "either or both" of the elements so conjoined, i.e., elements that are conjunctively present in some cases and disjunctively present in other cases. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the term "about" is used in conjunction with a numerical range, it modifies that range by extending the boundaries above and below those numerical values. In general, the term "about" is used herein to modify a numerical value above and below the stated value by a variance of 20%, 10%, 5%, or 1%. In certain embodiments, the term "about" is used to modify a numerical value above and below the stated value by a variance of 10%. In certain embodiments, the term "about" is used to modify a numerical value above and below the stated value by a variance of 5%. In certain embodiments, the term "about" is used to modify a numerical value above and below the stated value by a variance of 1%.

When a range of values is listed herein, it is intended to encompass each value and sub-range within that range. For example, "1-5 ng" is intended to encompass 1 ng, 2 ng, 3 ng, 4 ng, 5 ng, 1-2 ng, 1-3 ng, 1-4 ng, 1-5 ng, 2-3 ng, 2-4 ng, 2-5 ng, 3-4 ng, 3-5 ng, and 4-5 ng.

It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

As used herein, "a food formulation" may be used interchangeably with "a food composition" and/or "a food supplement," throughout the specification and refer to the composition as described herein for the relief of symptoms associated with degenerative joint diseases in humans. The supplement may be in any form, including a solid form (e.g. a powder), a semi-solid form (e.g. a food-like consistency/gel), or a liquid form. Further, the supplement may be in the form of a tablet or a capsule. The liquid can conveniently be mixed in with food or ingested directly (e.g., via a spoon or via a pipette-like device). The supplement may be high in one or more components of the invention or may be in the form of a combined pack of at least two parts, each part containing the required level of one or more component.

In certain embodiments, the disclosed food formulation can be in the form of a concentrate that is diluted prior to use. In certain embodiments, the food formulation can be supplemented with a pharmaceutical composition (e.g. a medicament for the treatment of the degenerative joint disease).

The food supplement disclosed herein encompasses any product that a human may consume in his/her diet. Thus, the disclosure covers standard food products, as well as snack products (e.g., snack bars, biscuits, sweet products, etc.). The foodstuff is preferably a cooked product. It may incorporate a meat or an animal-derived material (such as beef, chicken, turkey, lamb, etc.). The foodstuff alternatively may be meat-free (preferably including a meat substitute, such as soya, maize gluten, or a soya product) in order to provide a source of protein.

The product may contain additional protein sources, such as soya protein concentrate, milk proteins, gluten, etc. The product may also contain a starch source, such as one or more grains (e.g. wheat, corn, rice, oats, barley, etc.) or may be starch-free.

The term "therapeutically effective amount" as used herein refers to its meaning as is generally accepted in the art. The term generally refers to the amount of the food formulation that will elicit the requisite biological response in the human. For example, if a given treatment is considered effective when there is at least about a 25% reduction in a measurable parameter associated with a disease or disorder, a therapeutically effective amount of a drug for the treatment of that disease or disorder is that amount necessary to effect at least about a 25% reduction in that parameter.

The terms "administer," "administering," or "administration" are used herein in their broadest sense. These terms refer to any method of delivering a food supplement as described herein to the human. In a preferred embodiment, the food supplement is administered orally to the human.

Terms such as "treating," "treatment," "to treat," "alleviating," or "to alleviate" as used herein refer to both (1) therapeutic measures that cure, slow down, lessen symptoms of, and/or halt progression of a diagnosed pathologic condition or disorder (e.g., the degenerative joint disease) and (2) prophylactic or preventative measures that prevent or slow the development of a targeted pathologic condition or disorder (e.g., "preventing" or "to prevent"). Thus, the humans in need of treatment include those already with the disorder, those prone to have the disorder, and those in whom the disorder is to be prevented.

Cartilage

Cartilage is a firm, pressure-stable support tissue, which consists of water-rich cartilage cells and an intercellular substance. Cartilage tissue develops from the mesenchymal cells of the embryo. The cells are rich in glycogen and lie close together. Due to the formation of the intercellular substance (matrix), they move ever further apart. The matrix consists of a network of collagen fibrils which are embedded in a hydrogel of extremely large aggregates of proteoglycans and hyaluronic acid and weakly basophilic basic substances. See, M. Sittinger, et al., "Engineering of Cartilage Tissue Using Bioresorbable Polymer Carriers in Perfusion Culture," Biomaterials, 1994, 15(6), Pages 451-456.

Chondroblasts, or perichondrial cells, are the mesenchymal progenitor cells in situ which, from endochondral ossification, will form chondrocytes in the growing cartilage matrix. The growth of the cartilage takes place through the continuous production of intercellular substance and the mitosis of the chondroplasts, or a dividing cell of growing cartilage tissue, which results in the complete cartilage tissue. In addition to its structural and physical properties, the extracellular matrix plays a central role in different cell activities. See, Sittinger, et al., 1994. At the same time, the perichondrium, the cartilage skin, differentiates on the surface of the cartilage. This leads to the formation of the synovial joint lubrication See, L. Dintenfass, "Lubrication in Synovial Joints," Nature, 1963, 197, Pages 496-497.

The cartilage tissue does not show any blood vessels (e.g., is anavascular) or nerve structures (e.g., is aneural). Nutrition is supplied to the chondrocytes by diffusion from the perichondrium and the synovial. The compression of articular cartilage or flexion of elastic cartilage generates fluid flow, which assists diffusion of nutrients to the chondrocytes. Cartilage cells (chondrocytes) are responsible for matrix synthesis and degradation. Chondrocytes have an active metabolism. However, the overall metabolic activity of chondrocytes is not very high due to the low cell density. See, Casper Bindzus Foldager, "Cell Seeding Densities in Autologous Chondrocyte Implantation Techniques for Cartilage Repair," Cartilage, 2012, 3(2), Pages 108-117. Moreover, compared to other connective tissues, cartilage has a very slow turnover of its extracellular matrix and does not repair. As such, the ability to regenerate cartilaginous tissue is severely restricted.

Forms of Cartilage

Three forms of cartilage tissue may be found in the human body, which include: hyaline cartilage, elastic cartilage, and fibrocartilage. Hyaline cartilage is the most common form of cartilage tissue and is of particular interest in medicine, since it can show signs of wear due to strong mechanical stress. Hyaline cartilage is an intercellular tissues that consists of an amorphous basic substance and contains no nerves or blood vessels. Hyaline cartilages has collagen fibers embedded into it, which provides structures, such as the larynx, trachea, articulating surfaces of bones, etc., a definite form, while restricting mobility and flexibility. Specifically, the cartilage tissue of the hyaline cartilage consists of chondrocytes (approximately 1-10%), water (approximately 65-85%), collagens (approximately 10-25%), and proteoglycans (approximately 5-10%).

If chondroplasts dies, bone-forming cells (osteoblasts) develop in their place. This enables it to grow in length up to adult size. After growth has stopped, it remains at the joint-forming bone ends, where it covers it as an approximately 2 mm thick joint cartilage. The mechanical load is absorbed by various components of the cartilage tissue. A chondron is a chondrocyte and its associated pericellular microenvironment considered as a unit. The pressure-elastic elements represent the chondrons, which are kept under tension by tension-resistant wrapping and the entirety of the hydrated proteoglycan molecules.

When hyaline cartilage is on the articular surfaces of bones (the surfaces at joints), it is called articular cartilage. Articular cartilage functions as a shock absorber and also reduces friction between bones where they meet at joints. As a person ages, this cartilage can wear away, leading to joint pain and swelling that is sometimes only alleviated by surgery.

Elastic cartilage or "yellow cartilage" is a type of cartilage present in the outer ear, Eustachian tube, and epiglottis. The elastic cartilage is of great interest in plastic reconstructive medicine. Elastic cartilage contains elastic fiber networks, in addition to the substances of the hyaline cartilage. The elastic cartilage cells form chondrons. The chondrons are smaller and poorer in cells. The elastic cartilage cannot regenerate, but it doesn't ossify for that reason either.

Fibrocartilage consists of a mixture of white fibrous tissue (which provides toughness and inflexibility) and cartilaginous tissue (which provides elasticity) in various proportions. Fibrocartilage is the only type of cartilage that contains Type I collagen in addition to the normal type II collagen. Fibrocartilage is present in the soft tissue-to-bone attachments, pubic symphysis, the anulus fibrosus of intervertebral discs, menisci, the triangular fibrocartilage and the temporomandibular joints (TMJ).

Collagen

Collagen is the main structural protein in the extracellular matrix in various connective tissues in the body. See, K. E. Kadler, et al., "Collagens at a Glance," Journal of Cell Science, 2007, 120, Pages 1955-1958. Collagen may be fibrillar or non-fibrillar. Fibrillar collagen includes Type I, Type II, Type III, Type V, and Type XI. Non-fibrillar collagen includes fibril associated collagens with interrupted triple helices (or FACIT) (e.g., Type IX, Type XII, Type XIV, Type XIX, and Type XXI), short chain collagen (Type VIII and Type X), basement membrane collagen (e.g., Type IV), multiple triple helix domains with interruptions (or Multiplexin) (e.g., Type XV and Type XVIII), membrane associated collagens with interrupted triple helices (or MACIT) (e.g., Type XIII and Type XVII), and others (e.g., Type VI and Type VII).

The five most common types of collagen include Type I (e.g., the main component of the organic part of bone), Type II (e.g., the main collagenous component of cartilage), Type III (e.g., the component of reticular fibers), Type IV forms basal lamina, the epithelium-secreted layer of the basement membrane), and Type V (e.g., cell surfaces, hair, and placenta). Type I collagen makes up approximately 90% of the whole organism, whereas type II collagen is the main component of the extracellular matrix and accounts for 85-95% of the total collagen.

Extracellular Matrix of Cartilage

Cartilage extracellular matrix is composed primarily of Type II collagen and an interlocking mesh of fibrous proteins and proteoglycans, hyaluronic acid, and chondroitin sulfate. See, Yue, Gao, et al., "The ECM-Cell Interaction of Cartilage Extracellular Matrix on Chondrocytes," BioMed Research International, 2014, Pages 1-8. It should be appreciated that collagens and proteoglycans can take up to 98% of the cartilage tissue.

Articular cartilage extracellular matrix plays a crucial role in regulating chondrocyte metabolism and functions, such as organized cytoskeleton through integrin-mediated signaling via cell-matrix interaction. Cell signaling through integrins regulates several chondrocyte functions, including differentiation, metabolism, matrix remodeling, responses to mechanical stimulation, and cell survival. The major signaling pathways that regulate chondrogenesis have been identified as wnt signal, nitric oxide (NO) signal, protein kinase C (PKC), and retinoic acid (RA) signal. Integrins are a large family of molecules that are central regulators in multicellular biology. They orchestrate cell-cell and cell-matrix adhesive interactions from embryonic development to mature tissue function.

The functional integrity of articular cartilage is dependent on the maintenance of the extracellular matrix, a process which is controlled by chondrocytes. The regulation of the extracellular matrix biosynthesis is complex and a variety of substances have been found to influence chondrocyte metabolism. The presence of extracellular hydrolyzed collagen has been shown to lead to a dose dependent increase in Type II collagen secretion. However, native collagens, as well as a collagen-free hydrolysate of wheat proteins, have been shown to fail to stimulate the production of Type II collagen in chondrocytes. See, Steffen Oesser, et al., "Stimulation of Type II Collagen Biosynthesis and Secretion in Bovine Chondrocytes Cultured With Degraded Collagen," Cell Tissue Res., 2003, 311(3), Pages 393-399. These results indicate a stimulatory effect of degraded collagen on Type II collagen biosynthesis of chondrocytes and suggest a possible feedback mechanism for the regulation of collagen turnover in cartilage tissue. See, Steffen Oesser, et al., 2003.

Specifically, proteoglycans have the ability to bind large amounts of water and are responsible for pressure elasticity. Proteoglycans can be compressed to 20% of their volume and consist of a core protein to which glycosaminoglycans are covalently attached. Proteoglycans can be extremely complex and heterogeneous in their structure with regard to protein content, molecular size, and number and types of glycosaminoglycans. The most common representatives in the matrix of the cartilage are chondroitin-4-sulfate, keratan sulfate, and hyaluronic acid, whereby hyaluronic acid is actually only a glycosaminoglycan without binding to a core protein.

Due to the interactions between the collagens, proteoglycans, and the water content, cartilage shows a viscoelastic behavior, which leads to an extremely strong biomechanical structure. During the synthesis of the matrix, the chondroitin sulfate secreted by the chondrocytes accumulates around the cells and forms the cartilage capsule. The chondron denotes the group of chondrocyte, capsule, and cell yard in the extracellular matrix.

The structure of the cartilage from the surface of the cartilage to the subchondral bone can be divided into four zones—the tangential zone, the transition zone, the radial zone, and the mineralization zone. The tangential zone is on the surface in which the chondrocytes are flat and widely scattered, but have a high cell density. In the transition zone, the cells are rounder and arranged in small groups. In the thickest zone of the hyaline cartilage, the radial zone, the chondrocytes can be seen in columns. A basophilic boundary line separates the radial zone and mineralization zone, in which calcium crystals are formed.

The extracellular matrix of the different zones varies in the concentrations of water, collagens, and proteoglycans, and in the size of the aggregates. The cells of the different zones vary not only in size, shape and orientation, but also in metabolic activity. The response of the cartilage zones to mechanical stress may differ.

Joint Diseases

Arthropathy, or any disease of the joints, includes arthritis, Charcot joint, and diabetic hand syndrome, among others. Symptoms of arthropathy include joint inflammation, joint deterioration because of nerve damage, and limited movement. With increasing age, there is wear and tear of the articular cartilage, especially if there is a general axis deviation of the bones (bow leg or X leg), the body mass is disproportionately high or constant, long-term stress acts on the cartilage. This degenerative and destructive joint disease is called arthritis. With early primary arthritis, the cartilage becomes yellow and opaque with localized areas of softening and roughening of the surfaces. As degeneration progresses, the soft areas become cracked and worn, exposing bone under the cartilage. The bone then begins to remodel and increase in density, while any remaining cartilage begins to fray. Eventually, osteophytes (spurs of new bone) covered by cartilage form at the edge of the joint.

Degenerative joint diseases include, but are not limited to, osteochondrosis and degenerative arthritis (or osteoarthritis). Symptoms of degenerative joint disease include joint swelling, muscle atrophy, pericapsular fibrosis, and crepitation. Radiographic changes in the joint include joint effusion, periarticular soft-tissue swelling, osteophytosis, subchondral bone sclerosis, and possibly narrowed joint. Degenerative joint disease can occur at any joint in the human's body, without limitation.

More specifically, osteochondrosis is a disturbance in endochondral ossification that is sometimes classified as dyschondroplasia. It may involve the separation of the immature articular cartilage from the underlying epiphyseal bone, which sometimes dissects completely free and floats loose in the synovial cavity and results in accompanying synovitis, or it may result in the retention of pyramidal cores of physical cartilage projecting into the metaphysis. Often, these two lesions occur simultaneously in the same bone. The disease occurs during maximal growth when the biomechanical stresses are greatest in an immature skeleton of the human (e.g., in children or adolescents).

Osteoarthritis is a non-infectious progressive disorder of primarily the diarthrodial joints (e.g., the synovial weight-bearing joints). In osteoarthritis, there is a progressive deterioration of the articular cartilage characterized by hyaline cartilage thinning, joint effusion, and periarticular osteophyte formation. Joint degeneration can be caused by trauma, infection, immune-mediated diseases, or developmental malformations. The inciting cause initiates chondrocyte necrosis, release of degradative enzymes, synovitis, and continued cartilage destruction and inflammation.

With these diseases, as the mechanical wear increases, the cartilage needs repairing. The cartilage cells are unable to produce enough of the sponge-like matrix and therefore the damaged cartilage cannot repair itself. The cartilage has no blood supply to enhance healing. The majority of degenerative joint diseases is the result of mechanical instabilities or aging changes within the joint.

With age-related changes in the cartilage, the loss of chondrocytes and a deteriorated metabolic situation of the chondrocytes are responsible for the destruction. This could be the cause of poor synovial nutrition of the chondrocytes. Due to the metabolic disturbance of cell activity, inadequate proteoglycans are synthesized in modified form (e.g. shorter mucopolysaccharide chains). The result is a reduced water storage capacity, which leads to the unmasking of the collagen fibers. The elasticity of the cartilage is greatly reduced and there is a loss of cartilage substance.

The degree of cartilage damage differs and is divided into four different grades. Grade I refers to discoloration, softening, and swelling of the cartilage. Grade II refers to cracks in the cartilage and fraying of the cartilage. Grade III refers to defects down to the bones and cracks in the cartilage. Grade IV refers to exposed bone and complete absence of cartilage.

Hydrolyzed Collagen

Hydrolyzed collagen protein, particularly enzymatically hydrolyzed collagen, is described in U.S. Pat. No. 4,804,745 A, granted on Feb. 14, 1989 and WO 1998/044929 A1, published on Oct. 15, 1998, the contents of which are incorporated herein by reference in their entireties. It should be appreciated that "hydrolyzed collagen" is referred herein as "collagen hydrolysate," "gelatine," "gelatine hydrolysate," "hydrolyzed gelatine," and/or "collagen peptides."

The process of hydrolysis involves breaking down the molecular bonds between individual collagen strands and peptides using combinations of physical, chemical, or biological means. Hydrolyzed collagen may be obtained by the enzymatic hydrolysis of collagenous tissues (e.g., bone, hide, or hide split) from mammals. The main characteristic of hydrolyzed collagen is its amino acid composition, which is identical to Type II collagen, thus providing high levels of glycine and proline, which are two amino acids essential for the stability and regeneration of cartilage.

Hydrolyzed collagen is generally recognized as a safe food ingredient by regulatory agencies, as hydrolyzed collagen is well digested. Clinical use of hydrolyzed collagen is associated with minimal adverse effects and some gastrointestinal side effects, such as fullness and unpleasant taste.

In most scenarios, hydrolyzed collagen is administered alone in a water solution. However, hydrolyzed collagen may be well absorbed and digested in other food matrices, such as fermented milk. See, Stephane Walrand, et al., "Consumption of a Functional Fermented Milk Containing Collagen Hydrolysate Improves the Concentration of Collagen-Specific Amino Acids in Plasma," J. Agric. Food Chem., 2008, 56(17), Pages 7790-7795.

As used herein, "chondroprotective agents" refers to substances that protect articular cartilage during the course of osteoarthritis. When these chondroprotective agents appear to alter the course of the disease, these agents may be termed disease-modifying osteoarthritis drugs (or "DMOADs"). These chondroprotective agents may be compounds that delay progressive joint space narrowing characteristic of arthritis and improves the biomechanics of articular joints by protecting chondrocytes.

Some research has been done in animals to study the effects of chondroprotective agents for osteoarthritis. See, J. U. Carmona J U, et al., "Effect of the Administration of an Oral Hyaluronan Formulation on Clinical and Biochemical Parameters in Young Horses With Osteochondrosis," Vet Comp. Orthop. Traumatol., 2009, 22, Pages 455-459; C. L. Aragon, et al., "Systematic Review of Clinical Trials of Treatments for Osteoarthritis in Dogs," J. Am. Vet. Med. Assoc., 2007, 230, Pages 514-521; E. J. Durante, et al., "Aspects of Elbow Dysplasia in Dogs," Analecta Veterinaria, 1998, 18, Pages 59-70; R. D. Altman, et al., "Prophylactic Treatment of Canine Osteoarthritis With Glycosaminoglycan Polysulfuric Acid Ester," Arthritis Rheum., 1989, 32, Pages 759-766; C. R. Cook, et al., "Diagnostic Imaging of Canine Elbow Dysplasia: A Review," Vet Surg 2009, 38, Pages 144-153; and M. R. Carreno, et al., "The Effect of Glycosaminoglycan Polysulfuric Acid Ester on Articular Cartilage in Experimental Osteoarthritis: Effects on Morphological Variables of Disease Severity," J. Rheumatol., 1986, 13, Pages 490-497.

The STR/ort mouse is a well-recognized model which develops a natural form of osteoarthritis very similar to the human disease. An in vivo study with STR/ort mice that spontaneously developed osteoarthritis has shown that long-term hydrolyzed collagen supplementation may decrease osteoarthritis cartilage degeneration and delay the progression of osteoarthritis. See, S. Oesser, et al., "Prophylactic Treatment with a Special Collagen Hydrosylate Decreases Cartilage Tissue Degeneration in the Knee Joints." OA and Cartilage, 2008, 16(4) Page S45; Alfonso E. Bello, et al., "Collagen Hydrolysate for the Treatment of Osteoarthritis and Other Joint Disorders: A Review of the Literature," Curr. Med. Res. Opin., 2006, 22(11), Pages 2221-2232; and R. W. Moskowitz, "Role of Collagen Hydrolysate in Bone and Joint Disease," Semin. Arthritis Rheum., 2000, 30(2), Pages 87-99. These results are in favor of a disease modifying effect of hydrolyzed collagen and its potential efficacy in osteoarthritis.

The chondroprotective effect of hydrolyzed collagen was also confirmed in another study investigating both the in vitro and in vivo effect in mice. See, S. Nakatani, et al., "Chondroprotective Effect of the Bioactive Peptide Prolyl-Hydroxyproline in Mouse Articular Cartilage in Vitro and in Vivo," Osteoarthritis Cartilage, 2009, 17(12), Pages 1620-1627. Hydrolyzed collagen was demonstrated to protect cartilage against degradation induced by phosphorus injection. The same study showed that hydrolyzed collagen prevented chondrocyte differentiation into mineralized chondrocytes.

Another study investigated the effect of hydrolyzed collagen supplementation in healthy adult humans without degenerative joint disease, but with joint pain. This study showed that a hydrolyzed collagen dietary supplement can improve joint pain and mobility, and can reduce analgesic medication in healthy active adults without degenerative joint disease. See, Kristine L. Clark, et al., "24-Week Study on the Use of Collagen Hydrolysate as a Dietary Supplement in Athletes with Activity-Related Joint Pain," Curr. Med. Res. Opin., 2008, 24(5), Pages 1485-1496. The hydrolyzed collagen supplementation can then improve knee function during joint-stressing activities. These observations were also reported in a scientific communication in patients with symptomatic mild osteoarthritis. See, L. Zuckley, et al., "Collagen Hydrolysate Improves Joint Function in Adults With Mild Symptoms of Osteoarthritis of the Knee," Medicine & Science in Sports & Exercise, 2004, 36(5) Page 5153-5154.

Another reference mentioned a better effect of hydrolyzed collagen compared to placebo in severe osteoarthritis patients than in the overall studied population. See, R. W., "Role of Collagen Hydrolysate in Bone and Joint Disease," Semin. Arthritis Rheum., 2000, 30(2), Pages 87-99. More recently, another relevant study showed joint function improvement after hydrolyzed collagen treatment in patients with primary osteoarthritis, which is mostly related to aging. See, P. Benito-Ruiz, et al., "A Randomized Controlled Trial on the Efficacy and Safety of a Food Ingredient, Collagen Hydrolysate, for Improving Joint Comfort," Int. J. Food Sci. Nutr., 2009, 60, Pages 99-113.

As can be seen, the use of oral chondroprotective agents for treating joint diseases such as osteoarthritis in humans and animals has been widely studied, and the synergistic effects of different nutraceuticals is a step forward in the management of osteoarthritis. See, Stefania D'Adamo, et al., "Nutraceutical Activity in Osteoarthritis Biology: A Focus on the Nutrigenomic Role," Cells, 2020, 9(1232), Pages 1-24; and Laurent G. Ameye, et al., "Osteoarthritis and Nutrition. From Nutraceuticals to Functional Foods: A Systematic Review of the Scientific Evidence," Arthritis Res. Ther., 2006, 8(4), Pages R127. However, a therapeutic effect has not been clearly proven.

Moreover, few studies have investigated the use of these reagents as prophylactics. As defend herein, a "prophylactic" is a medicine or course of action used to prevent disease. See, K. A. Kirkby, et al., "Canine Hip Dysplasia: Reviewing the Evidence for Nonsurgical Management," Vet Surg, 2012, 41, Pages 2-9; G. R. Bouck, et al., "A Comparison of Surgical and Medical Treatment of Fragmented Coronoid Process and Osteochondritis Dissecans of the Canine Elbow," Vet Comp Orthop Traumatol, 1995, 8, Pages 177-183; J. J. de Haan, et al., "Evaluation of Polysulfated Glycosaminoglycan for the Treatment of Hip Dysplasia in Dogs," Vet Surg, 1994, 23, Pages 177-181; and G. Lust, et al., "Effects of Intramuscular Administration of Glycosaminoglycan Polysulfates on Signs of Incipient Hip Dysplasia in Growing Pups," Am. J. Vet. Res., 1992, 53, Pages 1836-1843.

Food Formulation

Considering that joints with dysplasia usually show signs of osteoarthritis and administration of a chondroprotector (e.g., a chondroprotective agent or compound) may ameliorate the progression of clinical osteoarthritis symptoms, a food formulation is provided herein.

The food formulation may include a mixture of hydrolyzed collagen, hyaluronic acid, glucosamine hydrochloride, and ascorbic acid. The food formulation may also include a cannabinoid or prodrug thereof and/or a vitamin composition. In other examples, the food formulation may include an extracellular matrix composition and a vitamin composition and/or a cannabinoid or prodrug thereof. The extracellular matrix composition may comprise hydrolyzed collagen, hyaluronic acid, and glucosamine or pharmaceutically acceptable salts thereof. The food formulation may provide means of prevention and relief for humans that are susceptible to develop, or that have already developed, a degenerative joint disease (e.g., arthritis). The formulation facilitates the supply of nutrients to articular cartilage, promotes the biosynthesis of joint cartilage and attenuates chronic pain, joint inflammation and other symptoms caused by arthritis.

Extracellular Matrix Composition

Hydrolyzed Collagen

In certain embodiments, the hydrolyzed collagen protein can have a molecular weight in the range of about 1 to about 300 kD. In certain embodiments, the hydrolyzed collagen protein can have a molecular weight of about 10, about 50, about 100, about 150, about 200, about 250 or about 300 kD. In certain embodiments, the hydrolyzed collagen can have an average molecular weight of about 10, about 20, about 30, about 40, about 50, about 60, about 70, about 80, about 90 or about 100 kD. Higher molecular weight preparations are generally less readily soluble.

In a preferred embodiment, the hydrolyzed collagen is porcine collagen. Hydrolyzed porcine collagen powder is commercially available, e.g., from Summit Nutritionals. The powder has a particle size that passes through an 80-mesh sieve. It is 100% BSE free and comes from USDA approved sources.

In certain embodiments, the food formulation can contain about 1%, about 2%, about 3%, about 4%, about 5%, about 6%, about 7%, about 8%, about 9% or about 10% of hydrolyzed porcine collagen. In certain embodiments, the food formulation can contain 95%, 90%, 85%, 80%, 75%, 70%, 65%, 60%, 55%, 50%, 45%, 40%, 35%, 30%, 25%, 20%, 15%, 10%, 5% or less of hydrolyzed porcine collagen. In certain embodiments, the food formulation can contain about 99%, 98%, 97%, 96%, 95%, 94%, 93%, 92%, 91% or 90% w/w of hydrolyzed porcine collagen.

Preparation of Hydrolyzed Collagen

Figure 3:
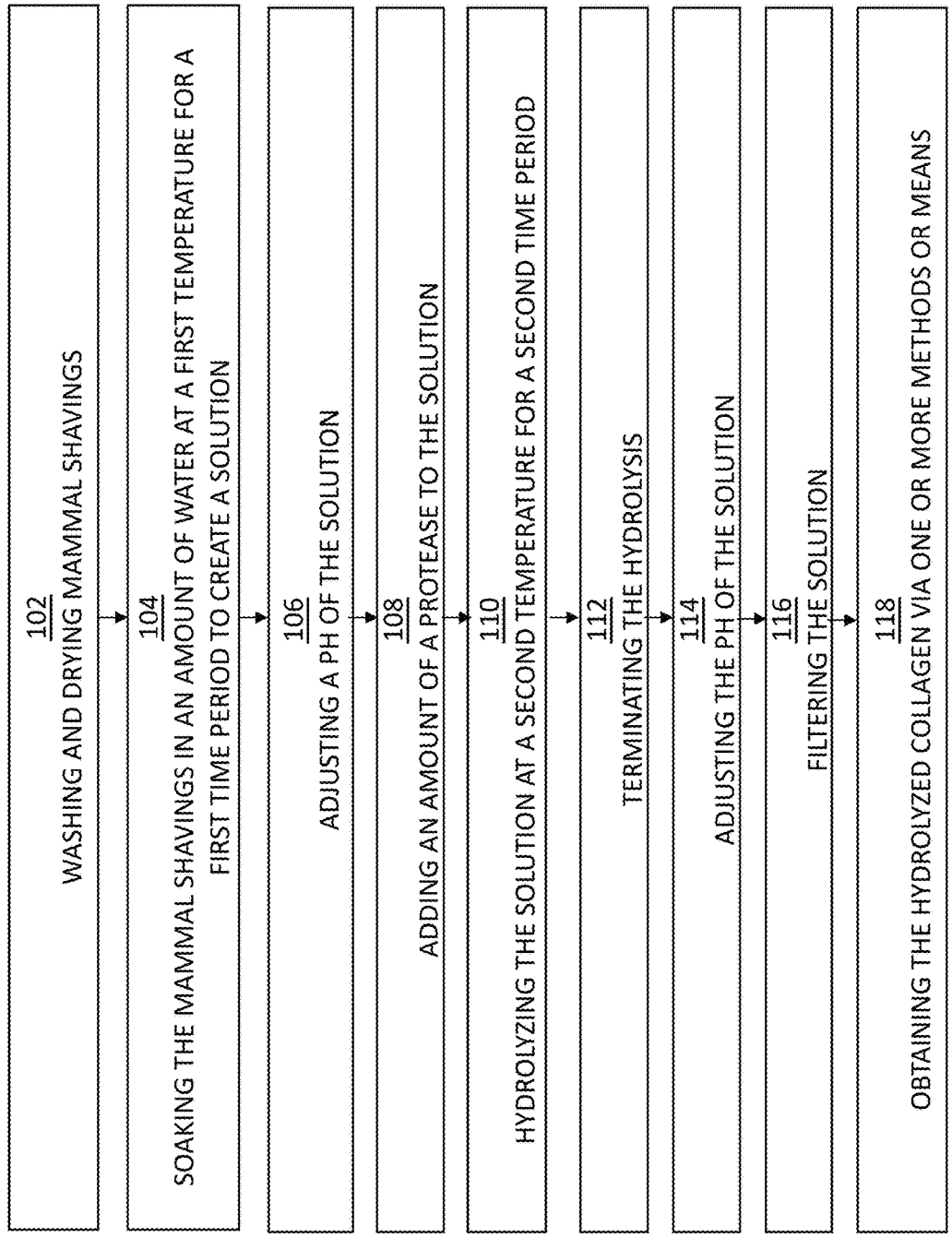
FIG. 3 depicts a method for enzymatic hydrolysis of collagen with a protease to create a hydrolyzed collagen, the hydrolyzed collagen being used in a food supplement, according to at least some embodiments described herein.

In other examples, the hydrolyzed collagen may be prepared by the following method, as shown in FIG. 3. The method begins at a process step 102 that includes washing and drying mammal shavings. A process step 104 follows the process step 102 and includes soaking the mammal shavings in an amount of water at a first temperature for a first time period to create a solution. A process step 106 follows the process step 104 and includes adjusting a pH of the solution. A process step 108 follows the process step 106 and includes adding an amount of the protease to the solution. A process step 110 follows the process step 108 and includes hydrolyzing the solution at a second temperature and for a second time period.

A process step 112 follows the process step 110 and includes terminating the hydrolysis. A process step 114 follows the process step 112 and includes adjusting the pH of the solution. A process step 116 follows the process step 114 and includes filtering the solution. A process step 118 follows the process step 116 and includes dialyzing the filtrate at a third temperature for a third time period. A process step 120 follows the process step 118 and includes obtaining the hydrolyzed collagen via one or more methods or means. The process step 120 ends the method of FIG. 3.

A specific example utilizing the method of FIG. 3 includes, at the process step 102, washing and drying mammal shavings (such as pigskin or porcine skin shavings). Then, the pigskin shavings may be cut into strips approximately 2-3 cm in length and approximately 2-6 mm in width. The process step 104 includes soaking the mammal shavings in an amount of water (approximately nine-fold water (w/v)) at a first temperature (approximately 60° C.) for a first time period (approximately 30 minutes) to create the solution and to slightly denature collagen fibers of the mammal shavings.

The process step 106 includes adjusting a pH of the solution to an optimal pH of the protease with 1 M hydrochloric acid (HCl) or 1 M sodium hydroxide (NaOH). It should be appreciated that in some examples, the protease may be Alcalase®, which is a liquid enzyme preparation containing a protease suitable for use in high temperature, moderate pH, detergent products. Alcalase® is produced by submerged fermentation of a selected strain of Bacillus licheniformis. The protease is not limited to this example provided herein and other examples are contemplated by Applicants' disclosure.

The process step 108 includes adding an amount of the protease (e.g., in a range between approximately 700 U/g pigskin to approximately 800 U/g pigskin) to the solution. In some examples, the amount of the protease is approximately 762 U/g pigskin. The process step 110 includes hydrolyzing the solution at a second temperature (e.g., the optimal temperature for the given protease) and for a second time period (e.g., approximately four hours) under stirring conditions.

The process step 112 includes terminating the hydrolysis by inactivating the protease at approximately 100° C. for approximately 5 minutes. The process step 114 includes adjusting the pH of the solution to a pH of 7 after the solution is cooled. The process step 116 includes filtering the solution. The process step 118 includes dialyzing the filtrate at a third temperature (e.g., room temperature) for a third time period (e.g., approximately 48 hours) to remove salt. The process step 120 includes obtaining the hydrolyzed collagen via one or more methods or means, such as vacuum freeze-drying.

Degree of Collagen Hydrolysis

Collagen hydrolysis is the breakage of amide bonds on a collagen peptide chain. Every mole of the amide bond that is broken produces 1 mol of free amino groups. Therefore, the degree of collagen hydrolysis has a positive correlation with the free amino content of hydrolyzed collagen. The free amino content of hydrolyzed collagen may be determined by using a formaldehyde titration method.

As an example, approximately 0.05 grams of hydrolyzed collagen is dissolved in approximately 60 mL of degassed distilled water. The pH may then be adjusted to a pH of 8.2 by addition of a 0.01 M NaOH solution under magnetic stirring. Then, approximately 20 mL of formaldehyde may be added slowly to the solution. After mixing the solution for approximately 3 minutes, the pH of solution may be titrated to a pH of 9.2 by a 0.1 M NaOH solution. The consumed volume of 0.1 M NaOH solution may be recorded as V1 (measured in mL). The free amino content of the hydrolyzed collagen (C, mmol/g) may be calculated according to the following equation:

$$C = 0.1 \times (V1 - V2)/0.05 \qquad \text{[Equation 1]}$$

Molecular Weight Distribution of Hydrolyzed Collagen

Molecular weight distribution of hydrolyzed collagen may be determined by centrifugal ultrafiltration. Briefly, hydrolyzed collagen may be dissolved in distilled water to obtain a concentration of 1 g/L and may then be filtered through membranes with approximately 0.45 μm pore diameter. Approximately 10 mL of the hydrolyzed collagen solution is then transferred to a centrifugal ultrafiltration filter with a fixed molecular weight cutoff (MWCO=3, 10, and 30 kDa), and centrifuged at approximately 4000 ×g in a swing bucket rotor at room temperature for approximately 45 minutes. Next, the hydrolyzed collagen with molecular weight lower than the MWCO can be ultra-filtered and recovered in a centrifuge tube. The concentration of the hydrolyzed collagen in the original solution (C0, mg/mL) and in the filtrate (C, mg/mL) can be determined by using a liquid total organic nitrogen (TON) analyzer (Elementar, Germany).

The concentration of the organic nitrogen in the hydrolyzed collagen solution before and after ultrafiltration is determined first, and then the concentration of the hydrolyzed collagen may be calculated though multiplying by the collagen N conversion index of 5.54. Following this, the hydrolysate mass (in mg) in each molecular weight fraction (<3, 3-10, 10-30, and >30 kDa) can be obtained, and the mass percentage of each fraction can be calculated. For example, the mass percentage of the 3-10-kDa fraction is given by the following equation:

$$(C10 V10 - C3 V3) \times 100/(10 \times C0) \qquad \text{[Equation 2]}$$

The free amino content of hydrolyzed collagen has a positive correlation with the broken-peptide bond content of collagen after a hydrolysis reaction, and can thus be used to evaluate the degree of collagen hydrolysis. See, P. M. Nielsen, et al., "Improved Method for Determining Food Protein Degree of Hydrolysis," Journal of Food Science, 2006, 66(5), Pages 642-646.

The basic amino acid residues predominant in pigskin (or porcine) collagen are lysine, arginine, and histidine, which accounts for approximately 8% of the total amino acid content. See, Xinhua Liu, et al., "Preparation and Characterization of an Advanced Collagen Aggregate From Porcine Acellular Dermal Matrix," International Journal of Biological Macromolecules, 2016, 88, Pages 179-188; and Toshiyuki Ikoma, et al., "Physical Properties of Type I Collagen Extracted From Fish Scales of Pagrus Major and Oreochromis Niloticas," International Journal of Biological Macromolecules, 2003, 32(3-5), Pages 199-204.

The protease Alcalase® has broad specificity and can destroy almost all of the peptide bonds in collagen, due to which collagen can be degraded into soluble peptides with the structure Gly-Pro-X (where X represents an amino acid residue). See, N.J. Adamson, et al., "Characterization of Casein Phosphopeptides Prepared Using Alcalase: Determination of Enzyme Specificity," Enzyme and Microbial Technology, 1996, 19(3), Pages 202-207; and Karl E. Kalder, et al., "Collagens At a Glance," Journal of Cell Science, 2007, 120, Pages 1955-1958. Thus, the degree of collagen hydrolysis by Alcalase® may be high and the hydrolyzed collagens with relatively low molecular weight were obtained. In conclusion, the hydrolyzed collagens with relatively high molecular weight, medium molecular weight, and low molecular weight can be separately prepared by using enzymatic hydrolysis methods.

Bioavailability of Hydrolyzed Collagen Solution

Several investigations showed a positive influence of orally administered gelatin on degenerative diseases of the musculo-skeletal system. Both the therapeutic mechanism and the absorption dynamics, however, remain unclear. The absorption of gelatin hydrolysate in its high molecular form, with peptides of 2.5-15 kD, may be detected following intestinal passage. These results demonstrate intestinal absorption and cartilage tissue accumulation of gelatin hydrolysate and suggest a potential mechanism for previously observed clinical benefits of orally administered gelatin. See, Steffen Oesser, et al., "Oral Administration of 14C Labeled Gelatin Hydrolysate Leads to an Accumulation of Radioactivity in Cartilage of Mice (C57/BL)," The Journal of Nutrition, 1999, 129(10), Pages 1891-1895.

Collagen is characterized by its high content of glycine, proline, and hydroxyproline, and is found to exert beneficial effects on joint pain related to activity and osteoarthritis. However, to exert any beneficial effects, it is essential that collagen is optimally absorbed. A study to investigate the postprandial absorption of collagen and to elucidate the impact of an exogenous enzymatic hydrolysis on absorption rate and bioavailability was conducted. Such study is depicted in FIG. 4.

Figure 4:
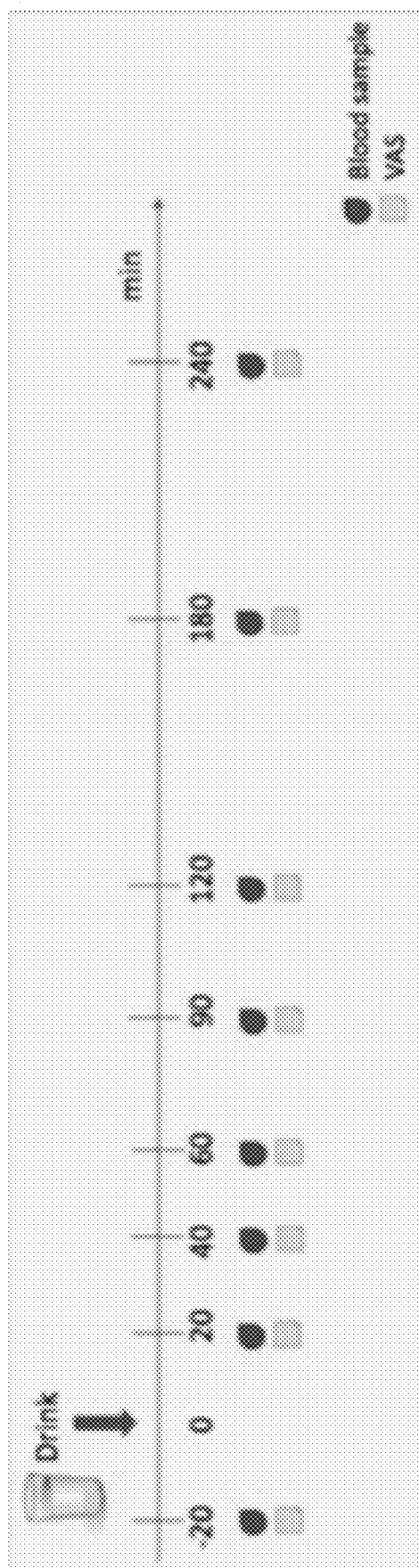
FIG. 4 depicts a schematic diagram of a study to investigate postprandial absorption of collagen and to elucidate an impact of an exogenous enzymatic hydrolysis on an absorption rate and bioavailability, according to at least some embodiments described herein.

The study of FIG. 4 was a randomized, blinded, crossover study where 10 healthy male subjects and 10 healthy female subjects received either 35 grams enzymatically hydrolyzed collagen protein, 35 grams non-enzymatically hydrolyzed collagen protein, or 250 mL of water as a placebo on three non-consecutive days. Blood samples were drawn before, and up to 240 minutes following ingestion. The blood metabolome (that includes the plasma and the red blood cells) was characterized by nuclear magnetic resonance (NMR)-based metabolomics. According to the study, a significant increase in the plasma concentration of nearly all amino acids was be observed over the 240 minute period for both the enzymatically hydrolyzed collagen protein and the non-enzymatically hydrolyzed collagen protein. In addition, the absorption rate and bioavailability of glycine, proline, and hydroxyproline were found to be significantly higher for the enzymatically hydrolyzed collagen protein.

Addition of Molecules to Hydrolyzed Collagen

In order to provide a nutraceutical that will enhance joint health and bone density, several other components may be added to the hydrolyzed collagen that are proven to increase matrix formation and moisture of the synovial fluid around the cartilage. The nutraceuticals may include: hyaluronic acid, glucosamine hydrochloride, ascorbic acid, cholecalciferol (Vitamin D), and/or d-alpha tocopheryl acetate (Vitamin E acetate), among others.

Glucosamine

Glucosamine and pharmaceutically acceptable salts thereof are commercially available, and are described in U.S. Pat. No. 5,587,363 A, granted on Dec. 24, 1996 and U.S. Pat. No. 5,364,845 A, granted on Nov. 15, 1994, the contents of which are incorporated herein by reference in their entireties. The primary source of exogenous glucosamine is the exoskeleton of shellfish and exists primarily in the form of glucosamine sulfate and glucosamine hydrochloride. Glucosamine and its pharmaceutically acceptable salts in combination with hydrolyzed collagen protein, provide the primary substrates for both collagen and proteoglycan synthesis including chondroitin sulfates and hyaluronic acid.

In a preferred embodiment, the glucosamine is in a salt form so as to facilitate its delivery and uptake in the gastrointestinal tract after oral ingestion. The preferred salt form is glucosamine hydrochloride. A significant portion of the ingested glucosamine localizes to cartilage and joint tissues, where it remains for long time periods. This indicates that oral administration of glucosamine reaches connective tissues, where glucosamine is incorporated into newly-synthesized connective tissue.

The primary source of exogenous glucosamine is the exoskeleton of shellfish and exists in primarily two formulations, glucosamine hydrochloride (HCl) and glucosamine sulfate. Glucosamine sulfate requires compound stabilizers in the form of salts and has 74% purity. Glucosamine HCl lacks the sulfate group and has 99% purity. In a preferred embodiment, the food formulation comprises glucosamine HCl.

Glucosamine administered orally is readily absorbed by the gastrointestinal tract. It is then rapidly metabolized by the liver and eliminated through the feces and urine. Peak levels in the bloodstream are achieved within about 8 hours after oral ingestion. Although the mechanism of action of glucosamine is unknown, recent studies suggest it may act as an anti-inflammatory agent that reduces the amount of nuclear factor kappa beta induced by interleukin-1 (IL-1).

In certain embodiments, the food formulation can contain about 1%, about 2%, about 3%, about 4%, about 5%, about 6%, about 7%, about 8%, about 9% or about 10% w/w of glucosamine HCl. In certain embodiments, the food formulation can contain 1-10%, 1-20%, 1-30%, 1-40%, 1-50% of glucosamine HCl.

Hyaluronic Acid

Hyaluronic acid, also known as hyaluronan, hyaluronate, or sodium hyaluronate, is an abundant non-sulfated glycosaminoglycan that is present in all joint tissues. Hyaluronic acid is a naturally occurring linear polysaccharide composed of (3-1,4-linked D-glucuronic acid-((3-(3-1,3)-N-acetyl-D-glucosamine disaccharide units. In its native form, hyaluronic acid exists as a high molecular weight polymer (about 106-107 Da). In normal synovial fluid, the molecular weight of hyaluronic acid is between about $7 \times 10^6$ D to $7 \times 10^6$ Da, and the concentration is about 2-4 mg/ml.

Hyaluronic acid synthesized by synoviocytes is responsible for the viscoelastic properties of synovial fluid and plays a fundamental role in the maintenance of the trophic status of the cartilage. In joint disease, there is a reduction in both the concentration and molecular weight of hyaluronic acid. Inflammation oxidation stress enhances degradation of hyaluronan. Intra-articular injection of exogenous high molecular weight hyaluronic acid (>5×10$^6$ Da) improves function in subjects with osteoarthritis or rheumatoid arthritis.

In certain embodiments, the food formulation can contain about 1%, about 2%, about 3%, about 4%, about 5%, about 6%, about 7%, about 8%, about 9% or about 10% of hyaluronic acid or pharmaceutically acceptable salts thereof. In certain embodiments, the food formulation can contain about 0.1%, about 0.2%, about 0.3%, about 0.4%, about 0.5%, about 0.6%, about 0.7%, about 0.8%, about 0.9% or about 1% w/w of hyaluronic acid or pharmaceutically acceptable salts thereof.

Vitamin Composition

In certain embodiments, the food supplement may one or more vitamins. The vitamins may include ascorbic acid, vitamin C, vitamin D (e.g., cholecalciferol), vitamin E (e.g., D-alpha-tocopheryl acetate), and/or coenzyme Q10 (e.g. palm oil), among others not explicitly listed herein.

Vitamin C is a water-soluble substance and can be incorporated into the food supplement described herein. See, U.S. Published Patent Application No. 2003/0198661 A1, published on Oct. 23, 2003, the content of which is incorporated by reference herein in its entirety. Vitamin C is important for building cartilage, bones, and teeth. It helps to strengthen and tighten the collagen fibers. Indeed, vitamin C is essential for producing the collagen structure.

The vitamin C composition may be in any form. It may be liquid, semi-solid, or solid. Preferably it is a heat stable. The source of the vitamin C is not limiting. Preferred vitamin C sources include crystalline ascorbic acid (optionally pure), ethylcellulose coated ascorbic acid, calcium phosphate salts of ascorbic acid, ascorbic acid-2-monophosphate salt or ascorbyl-2-monophosphate with small traces of the disphosphate salt and traces of the triphophate salt, calcium phosphate, or for example, fresh liver.

In certain embodiments, the vitamin C can be in the form of trisodium L-ascorbic acid-2-monophosphate or sodium-calcium L-ascorbic acid-2-monophosphate, both of which are commercially available, e.g. from DSM, Netherlands, under the tradename STAY-C®50 and STAY-C®35, respectively. In certain embodiments, these salts can be present in the food supplement at a concentration of from about 0.001% by weight to about 5% by weight, preferably in a concentration of from about 0.01% by weight to about 3% by weight, more preferably in a concentration of from about 0.1% by weight to about 1% by weight.

In certain embodiments, the food formulation can contain about 25, 50, 75, 100, 150, 200, 250, or 300 IU of vitamin D. In certain embodiments, the food formulation can contain about 5, 10, 15, 20, 25, 30, 35, 40, 45, 50, 55, 60, 65, 70 or 75 mg of vitamin E (D-alpha-tocopheryl acetate). In certain embodiments, the food formulation can contain about 0.1-1% palm oil.

Cannabinoid Composition

A cannabinoid is a class of chemical compositions that activate cannabinoid receptors, which may affect the behavior of neurotransmitters in the brain. Cannabinoid receptors are defined herein to include cannabinoid receptor type 1 (CB1), cannabinoid receptor type 2 (CB2), and the acetylcholine receptor AChR. Ligands for these receptor proteins include the endocannabinoids (produced naturally in the body by animals), the phytocannabinoids (found in *cannabis* and some other plants), and synthetic cannabinoids (manufactured artificially). The most notable cannabinoid is the phytocannabinoid tetrahydrocannabinol (THC), the primary psychoactive compound in cannabis.

Cannabidiol (CBD) is another major constituent of the plant. There are at least 113 different cannabinoids isolated from cannabis, exhibiting varied effects. Phytocannabinoids may be found in cannabis and some other plants. Synthetic cannabinoids may be produced chemically. For example, a phytocannabinoid may be extracted from a plant including, but not limited to, *Cannabis sativa, Cannabis indica, Cannabis ruderalis, Echinacea purpurea, Echinacea angustifolia, Echinacea pallida, Acmella oleraca, Helichrysum umbraculigerum*, and *Radula marginata*.

Synthetic cannabinoids may encompass a variety of distinct chemical classes. These classes may include classical cannabinoids structurally related to tetrahydrocannabinol (THC). The synthetic cannabinoids may also encompass non-classical cannabinoids, such as cannabimimetics, including the aminoalkylindoles, 1,5-diarylpyrazoles, quinolines, and aryl sulphonamides as well as eicosanoids related to the endocannabinoids.

The most notable cannabinoid is the phytocannabinoid Δ9-tetrahydrocannabinol (THC), the primary psychoactive compound of cannabis. However, numerous other cannabinoids may be included in the composition with varied effects, including Δ8-tetrahydrocannabinol (THC), cannabidiol (CBD), cannabinol (CBN), and dodeca-2E,4E,8Z,10E/Z-tetraenoic-acid-isobutylamides are the most prevalent natural cannabinoids. Other common cannabinoids that may be used in the composition include, but are not limited to, cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), and cannabigerol monomethyl ether (CBGM). The dodeca-2E,4E,8Z,10E/Z-tetraenoic-acid-isobutylamides and other cannabinoids may be derived from species in the *echinacea* genus.

Food Additives

One or more food additives and/or flavorings may be added to the food supplement. Examples of such food additives and/or flavorings are non-limiting.

Food Formulation

The disclosed food formulation is not limited by any method of administering the food formulation to the human. For example, the disclosed food formulation can be combined with an orally ingestible additive to form a supplement or premix that is added to the food. For example, the disclosed food formulation can be added to a standard additive in form of a broth or broth equivalent, a paste or as a lyophilized material.

In some embodiments, the disclosed food formulation can be prepared as a fine particulate matter (e.g., having a particulate size of 0.25-0.5 mm, 0.125-0.250 mm, or 0.0625-0.125 mm in size, although larger and smaller particle sizes may also be used) that can be added to a food. The disclosed food formulation can be added to a carrier and/or encapsulated prior to addition to the food. In some embodiments, the disclosed food formulation (e.g., prepared as a fine particulate matter) is added directly to the food (e.g., by sprinkling a liquid broth containing the composition over the food or by adding a dry particulate form of the disclosed food formulation to the food).

The disclosed food formulation is not limited by the amount (e.g., on a weight/weight percentage basis or on a volume/volume percentage basis) of the disclosed food formulation added to the food (e.g., total mixed ration). In some embodiments, the disclosed food formulation can be administered as a proportion of total daily dry matter intake. For example, in some embodiments, the disclosed food formulation can be administered to the human as 1.5%-2.5% of the subject's total daily dry matter intake, although lesser (e.g., 1.25%, 1.0%, 0.75%, 0.5%, 0.25%, or less) and greater (e.g., 2.75%, 3%, 3.25%, 3.5%, 4%, or more) amounts of the disclosed food formulation may be administered.

Figure 2:
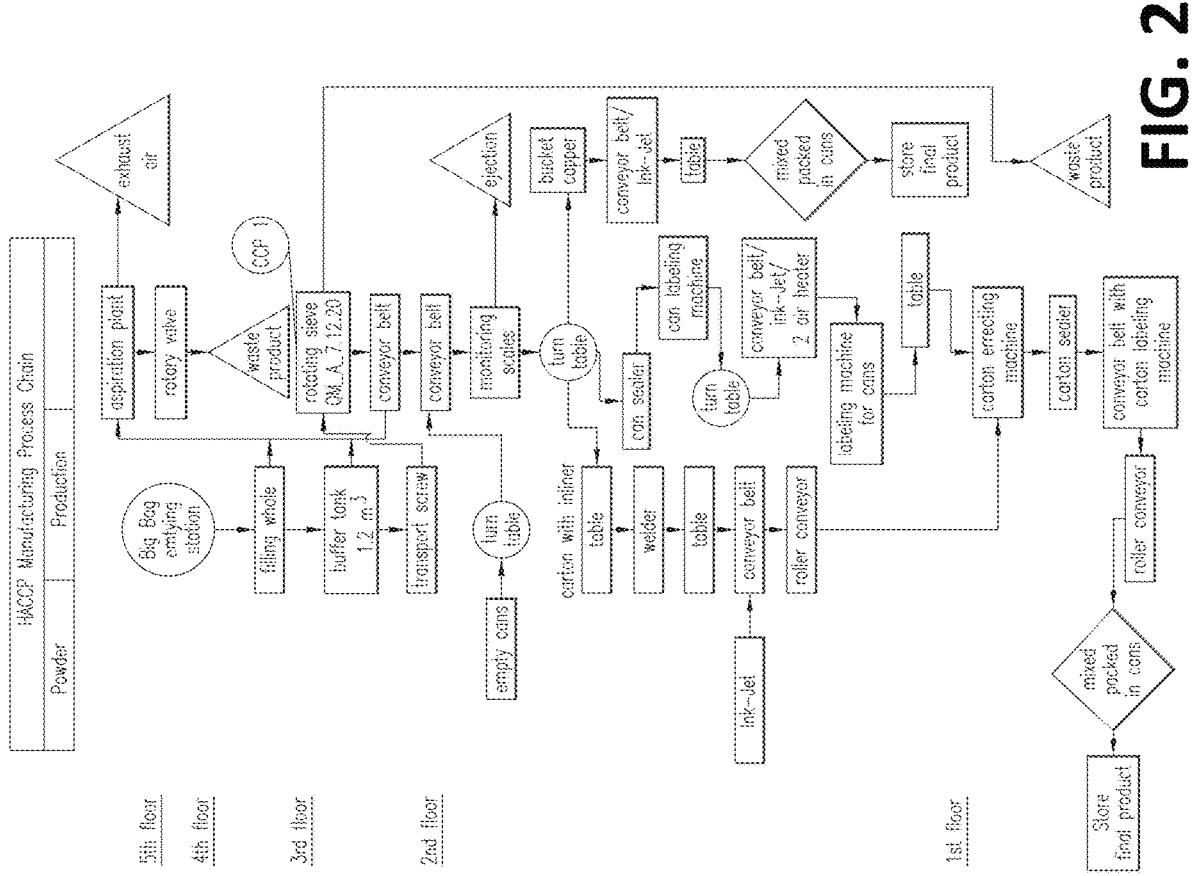
FIG. 2 depicts a hazard analysis and critical control point (HACCP) manufacturing process chain for final packaging of the disclosed food formulation, according to at least some embodiments described herein.

In a first example, the food supplement may be prepared as follows: 94% hydrolyzed porcine collagen, 5.9% glucosamine hydrochloride, 0.1% sodium hyaluronate, 0.1% palm oil (coenzyme Q10), additives, 1200 I.E. of vitamin D as cholecalciferol, 4.5 mg of vitamin E as D-alpha-tocopheryl acetate, and 30 mg of vitamin C as L-ascorbic acid. The steps of the manufacture process are disclosed in FIG. 1 and FIG. 2.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others or ordinary skill in the art to understand the embodiments disclosed herein.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A food supplement for a human, the food supplement consisting of:
    an extracellular matrix agent selected from the group consisting of: hydrolyzed porcine collagen, hyaluronic acid, and glucosamine or pharmaceutically acceptable salts thereof,
    and
    a cannabinoid composition, wherein the food supplement is effective in reducing at least one symptom of a degenerative joint disease in the human.

2. The food supplement of claim 1, wherein the at least one symptom of the degenerative joint disease in the human is selected from the group consisting of: joint pain and mobility pain.

3. A method to slow progression to at least one symptom of a degenerative joint disease in a human, the method comprising:
    administering a food supplement of claim 1.

4. The method of claim 3, wherein the cannabinoid composition includes a cannabinoid or prodrug thereof.

5. The method of claim 3, wherein the method further comprises administering a vitamin selected from at least one of vitamin C, vitamin D, and vitamin E.

6. A method to create a food supplement effective at reducing at least one symptom of a degenerative joint disease in a human, the method comprising:
    engaging in enzymatic hydrolysis of a porcine collagen with a protease to create a hydrolyzed porcine collagen; and
    adding a formulation to the hydrolyzed porcine collagen to create the food supplement of claim 1.

7. The method of claim 6, wherein the method further comprises: adding a vitamin composition
    wherein the vitamin composition is selected from the group consisting of: vitamin C, vitamin D, and vitamin E.

8. The method of claim 7, wherein the cannabinoid composition includes a cannabinoid or prodrug thereof.

9. The method of claim 8, wherein the enzymatic hydrolysis of the porcine collagen with the protease to create the hydrolyzed porcine collagen comprises:
    washing and drying mammal shavings;
    soaking the mammal shavings in an amount of water at a first temperature for a first time period to create a solution; and
    adjusting a pH of the solution before adding a protease.

10. The method of claim 9, wherein the mammal shavings comprise pigskin shavings.

11. The method of claim 9,
    wherein the amount of the water is nine-fold water (w/v),
    wherein the first temperature is approximately 60° C., and
    wherein the first time period is approximately 30 minutes.

12. The method of claim 9, wherein adjusting the pH of the solution is conducted with 1 M hydrochloric acid (HCl) or 1 M sodium hydroxide (NaOH).

13. The method of claim 9, wherein the enzymatic hydrolysis of the porcine collagen with the protease to create the hydrolyzed porcine collagen further comprises:
    adding an effective amount of the protease to the solution;
    hydrolyzing the pH-adjusted solution at a second temperature and for a second time period;
    terminating the hydrolysis;
    cooling the hydrolyzed solution;
    adjusting the pH of the hydrolyzed solution;
    filtering the pH-adjusted hydrolyzed solution;
    dialyzing the filtrate at a third temperature for a third time period; and
    obtaining the hydrolyzed porcine collagen.

14. The method of claim 13, wherein the effective amount of the protease comprises a range between approximately 700 U/g of the mammal shavings to approximately 800 U/g of the mammal shavings.

15. The method of claim 13,
    wherein the termination of the hydrolysis occurs by inactivating the protease at a fourth temperature for a fourth time period,
    wherein the fourth temperature is approximately 100° C., and
    wherein the fourth time period is approximately 5 minutes.

16. The method of claim 13, wherein adjusting the pH of the hydrolyzed solution occurs at a pH of 7.

17. The method of claim 13,
    wherein the second temperature is an optimal temperature for the protease,
    wherein the second time period is approximately 4 hours,
    wherein the third temperature is room temperature, and
    wherein the third time period is approximately 48 hours.

18. The method of claim 13, wherein the hydrolyzed porcine collagen is obtained via freeze-drying.

19. The food supplement of claim 1, wherein the food supplement contains about 99%, about 98%, about 97%, about 96%, about 95%, about 94%, about 93%, about 92%, about 91% or about 90% w/w of the hydrolyzed porcine collagen.

20. The food supplement of claim 19, wherein the food supplement contains about 94% w/w of the hydrolyzed porcine collagen.

* * * * *